United States Patent [19]

Sharifian et al.

[11] Patent Number: 5,709,790
[45] Date of Patent: Jan. 20, 1998

[54] ELECTROCHEMICAL PROCESS FOR PURIFYING HYDROXIDE COMPOUNDS

[75] Inventors: Hossein Sharifian; John E. Mooney, both of Austin, Tex.

[73] Assignee: Sachem, Inc., Austin, Tex.

[21] Appl. No.: 725,609

[22] Filed: Oct. 3, 1996

[51] Int. Cl.$^6$ ................................................. B01D 61/44
[52] U.S. Cl. ........................... 205/437; 205/445; 205/703; 205/770; 204/522; 204/523; 204/530; 204/534; 204/537; 204/541
[58] Field of Search ........................... 205/437, 445, 205/703, 770; 204/522, 523, 530, 534, 537, 541

[56] References Cited

U.S. PATENT DOCUMENTS

| | | | |
|---|---|---|---|
| 4,714,530 | 12/1987 | Hale et al. | 201/131 |
| 4,938,854 | 7/1990 | Sharifian et al. | 204/130 |
| 5,135,626 | 8/1992 | Mani et al. | 204/534 |
| 5,354,434 | 10/1994 | Satoh et al. | 204/72 |
| 5,389,211 | 2/1995 | Sharifian et al. | 204/72 |
| 5,405,508 | 4/1995 | Kawakami et al. | 204/102 |
| 5,575,901 | 11/1996 | Hulme et al. | 204/522 |

FOREIGN PATENT DOCUMENTS

| | | | |
|---|---|---|---|
| 60-131985 | 7/1985 | Japan | C25B 3/00 |
| 4228587 | 12/1990 | Japan | |
| 5106074 | 10/1991 | Japan | |

*Primary Examiner*—Arun S. Phasge
*Attorney, Agent, or Firm*—Renner, Otto, Boisselle & Sklar

[57] ABSTRACT

In one embodiment, the invention relates to a process for purifying solutions containing a hydroxide compound, including the steps of: (A) providing an electrochemical cell containing an anode, a cathode, a cation selective membrane and an anion selective membrane, wherein the cation selective membrane is positioned between the cathode and the anion selective membrane, and the anion selective membrane is positioned between the cation selective membrane and the anode, thereby defining a feed compartment between the cation selective membrane and the anion selective membrane, a recovery compartment between the cathode and the cation selective membrane, and a water compartment between the anion selective membrane and the anode; (B) charging a solution of an ionic compound at a first concentration to the water compartment, and water to the recovery compartment; (C) charging a solution of the hydroxide compound at a second concentration to the feed compartment; (D) passing a current through the cell to produce the hydroxide compound at a third concentration in the recovery compartment; and (E) recovering hydroxide compound from the recovery compartment.

21 Claims, 2 Drawing Sheets

ELECTROCHEMICAL PROCESS FOR PURIFYING HYDROXIDE COMPOUNDS

TECHNICAL FIELD

This invention relates to a method of purifying hydroxide compounds. In particular, the invention relates to a method of purifying or recycling organic and inorganic hydroxide compounds using an electrochemical cell.

BACKGROUND OF THE INVENTION

Quaternary ammonium hydroxides such as tetramethylammonium hydroxide (TMAH) and tetraethyl ammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium, potassium, zinc and calcium; anions such as halides, nitrates, nitrites, carbonates, carboxylates, sulfates and neutral organic species such as methanol, amines, etc. Particularly in recent years, there has been an increasing demand for quaternary ammonium hydroxides having a high purity.

U.S. Pat. No. 4,714,530 (Hale et al) describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

U.S. Pat. No. 4,938,854 (Sharifian et al) also describes an electrolytic process for purifying quaternary ammonium hydroxides by lowering the latent halide content. The electrolytic cell may be divided into an anolyte compartment and a catholyte compartment by a divider which may be an anion or cation selective membrane. The cathode in the catholyte compartment comprises zinc, cadmium, tin, lead, copper or titanium, or alloys thereof, mercury or mercury amalgam.

Japanese Kokai Patent No. 60-131985 (1985) (Takahashi et al) describes a method of manufacturing a high purity quaternary ammonium hydroxide in an electrolysis cell which is divided into an anode chamber and a cathode chamber by a cation exchange membrane. A quaternary ammonium hydroxide solution containing impurities is charged to the anode chamber and a direct current is supplied between two electrodes after water has been charged to the cathode chamber. Purified quaternary ammonium hydroxide is obtained from the cathode chamber. The purified quaternary ammonium hydroxide contains reduced amounts of alkali metals, alkaline earth metals, anions, etc.

SUMMARY OF THE INVENTION

In one embodiment, the present invention relates to a process for purifying or recycling solutions containing a hydroxide compound, including the steps of:

(A) providing an electrochemical cell containing an anode, a cathode, a cation selective membrane and an anion selective membrane, wherein the cation selective membrane is positioned between the cathode and the anion selective membrane, and the anion selective membrane is positioned between the cation selective membrane and the anode, thereby defining a feed compartment between the cation selective membrane and the anion selective membrane, a recovery compartment between the cathode and the cation selective membrane, and a water compartment between the anion selective membrane and the anode;

(B) charging a solution of an ionic compound at a first concentration to the water compartment, and water to the recovery compartment;

(C) charging a solution of the hydroxide compound at a second concentration to the feed compartment;

(D) passing a current through the cell to produce the hydroxide compound at a third concentration in the recovery compartment; and (E) recovering hydroxide compound from the recovery compartment.

In another embodiment, the present invention relates to a process for purifying or recycling solutions containing quaternary ammonium hydroxide, including the steps of:

(A) providing an electrochemical cell containing an anode, a cathode and one or more unit cells assembled for operational positioning between the anode and the cathode, each unit cell comprising; (A-1) three compartments defined by, in sequence beginning at the anode, an anion selective membrane and a cation selective membrane; (A-2) four compartments defined by, in sequence beginning at the anode, an anion selective membrane, a first cation selective membrane and a second cation selective membrane; or (A-3) four compartments defined by, in sequence beginning at the anode, a bipolar membrane, an anion selective membrane, and a cation selective membrane;

(B) charging a solution of an ionic compound at a first concentration to the compartment in each unit cell formed by the anion selective membrane and anode, the anion selective membrane and bipolar membrane, and the anode and bipolar membrane, and charging water to the compartment in each unit cell formed by the cathode and cation selective membrane, and the cation selective membrane and cation selective membrane;

(C) charging a solution of the quaternary ammonium hydroxide at a second concentration to the compartment in each unit cell formed by the cation selective membrane and anion selective membrane;

(D) passing a current through the cell to produce quaternary ammonium hydroxide at a third concentration in the compartment in each unit cell formed by the cathode and cation selective membrane; and (E) recovering quaternary ammonium hydroxide from the compartments in each unit cell formed by the cathode and cation selective membrane.

As a result of the methods of the claimed invention, recycled solutions of hydroxide compounds can be obtained in which the concentration and purity is increased. Recycling spent solutions of hydroxide compounds provides not only cost savings, but also environmental benefits by eliminating the need for synthesizing new hydroxide compound solutions and associated expensive purification processes. The relatively high concentration and purity of hydroxide compound solutions can effectively be used in numerous applications where hydroxide solutions are required.

DESCRIPTION OF THE PREFERRED EMBODIMENTS

Figure 1A:
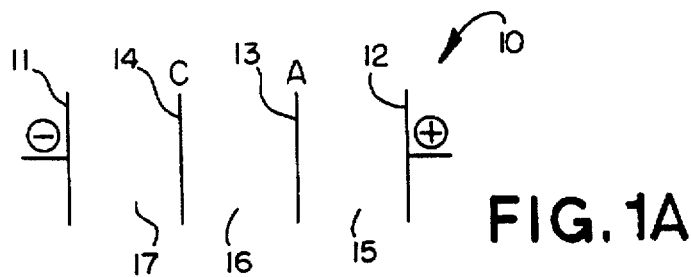
FIG. 1A is a schematic representation of a three-compartment of an electrochemical cell containing one unit cell in accordance with the invention.

The hydroxide compounds may generally be characterized by the formula $$A(OH)_x \quad (I)$$

wherein A is an organic or inorganic group and x is an integer equal to the valence of A. In one embodiment, the hydroxide compound should be sufficiently soluble in a solution such as water, alcohol or organic liquid, or mixtures thereof to allow a useful conversion rate.

Examples of inorganic hydroxide compounds, which can be purified in accordance with the present invention, include metal hydroxides, for instance the hydroxides of alkali metals such as sodium and potassium; alkaline earth metals such as magnesium and calcium; transition metals such as titanium, zirconium, chromium, manganese, iron, cobalt, nickel, copper, platinum; rare earth metals such as cerium, neodymium, samarium; etc. Specific examples of inorganic hydroxide compounds which can be purified in accordance with the process of the present invention include potassium hydroxide, magnesium hydroxide, ferrous hydroxide, ferric hydroxide, cuprous hydroxide, cupric hydroxide, cobaltous hydroxide, cobaltic hydroxide, etc.

In another embodiment the process of the present invention is useful in preparing purified organic hydroxide compounds such as quaternary ammonium hydroxides, quaternary phosphonium hydroxides and tertiary sulfonium hydroxides. These organic hydroxides may collectively be referred to as onium hydroxides. In this and other embodiments, A in Formula (I) above is an onium compound, and Formula (I) represents an onium hydroxide.

The quaternary ammonium and quaternary phosphonium hydroxides and may be characterized by the formula

wherein A is a nitrogen or phosphorus atom, $R_1$, $R_2$, $R_3$ and $R_4$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with A may form a heterocyclic group provided that if the heterocyclic group contains a C=A group, $R_3$ is the second bond.

The alkyl groups $R_1$ to $R_4$ may be linear or branched, and specific examples of alkyl groups containing from 1 to 20 carbon atoms include methyl, ethyl, propyl, butyl, pentyl, hexyl, heptyl, octyl, isooctyl, nonyl, octyl, decyl, isodecyl, dodecyl, tridecyl, isotridecyl, hexadecyl and octadecyl groups. $R_1$, $R_2$, $R_3$ and $R_4$ also may be hydroxyalkyl groups such as hydroxyethyl and the various isomers of hydroxypropyl, hydroxybutyl, hydroxypentyl, etc. In one preferred embodiment, $R_1$-$R_4$ are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

The quaternary ammonium hydroxides which can be purified in accordance with the process of the present invention may be represented by Formula III

wherein $R_1$-$R_4$ are as defined in Formula II. In one preferred embodiment, $R_1$-$R_4$ are alkyl groups containing from 1 to about 3 carbon atoms and hydroxyalkyl groups containing 2 or 3 carbon atoms. Most often the quaternary ammonium hydroxides purified in accordance with the process of the invention will be tetramethylammonium hydroxide (TMAH) or tetraethylammonium hydroxide (TEAH). Specific examples of other such hydroxides include tetramethylammonium hydroxide, tetraethylammonium hydroxide, tetrapropylammonium hydroxide, tetrabutylammonium hydroxide, tetra-n-octylammonium hydroxide, trimethylhydroxyethylammonium hydroxide, trimethylmethoxyethylammonium hydroxide, dimethyldihydroxyethylammonium hydroxide, methyltrihydroxyethylammonium hydroxide, phenyltrimethylammonium hydroxide, phenyltriethylammonium hydroxide, benzyltrimethylammonium hydroxide, benzyltriethylammonium hydroxide, dimethylpyrolidinium hydroxide, dimethylpiperidinium hydroxide, diisopropylimidazolinium hydroxide, N-alkylpyridinium hydroxide, etc.

Examples of quaternary phosphonium hydroxides representative of Formula II wherein A=P which can be purified in accordance with the process of the present invention include tetramethylphosphonium hydroxide, tetraethylphosphonium hydroxide, tetrapropylphosphonium hydroxide, tetrabutylphosphonium hydroxide, trimethylhydroxyethylphosphonium hydroxide, dimethyldihydroxyethylphosphonium hydroxide, methyltrihydroxyethylphosphonium hydroxide, phenyltrimethylphosphonium hydroxide, phenyltriethylphosphonium hydroxide and benzyltrimethylphosphonium hydroxide, etc.

In another embodiment, the tertiary sulfonium hydroxides which can be purified in accordance with this invention may be represented by the formula $$R_1-\overset{R_2}{\underset{R_3}{S^{\oplus}OH^{-}}} \qquad (IV)$$

wherein $R_1$, $R_2$ and $R_3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with S may form a heterocyclic group provided that if the heterocyclic group contains a C=S group, $R_3$ is the second bond.

Examples of the hydroxide compounds represented by Formula IV include trimethylsulfonium hydroxide, triethylsulfonium hydroxide, tripropylsulfonium hydroxide, etc.

The hydroxide compounds which are purified or recycled in accordance with the process of the present invention are mixtures, preferably solutions, containing an oxidizable liquid and from about 3% to about 55% by weight of the hydroxide and generally will contain varying amounts of one or more undesirable anions such as halide, carbonate, formate, nitrite, nitrate, sulfate, etc., some cations such as metals including zinc and calcium, sodium, potassium and some neutral species such as methanol, amines, etc. For example, solutions of quaternary ammonium hydroxides prepared by the electrolysis of quaternary ammonium halides typically may contain, at 25% by weight of quaternary ammonium hydroxide, from about 15 to about 500 ppm of halide and up to about 10,000 ppm of nitrate. Unless otherwise specifically indicated in this application all references to ppm of halide, metals, or carbonates, etc., are for solutions containing 25% by weight of the hydroxide compound.

In one embodiment, the process of the present invention is effective in reducing the amount of either nitrate or halide present in solutions of hydroxide compounds such as quaternary ammonium hydroxides. In a further embodiment, the process of the present invention results in a reduction of halide as well as nitrate in a solution of a hydroxide compound such as quaternary ammonium hydroxide.

Hydroxide compounds are commercially available. Alternatively, hydroxide compounds can be prepared from the corresponding salts such as halides, sulfates and the like. Various methods of preparation are described in U.S. Pat. Nos. 4,917,781 (Sharifian et al) and 5,286,354 (Bard et al) which are hereby incorporated by reference. There is no particular limit as to how the hydroxide compound is obtained.

In accordance with the process of the present invention, the hydroxide compound such as those described above are purified or recycled in an electrochemical cell. The purification or recyclization may be by electrolysis in an electrolytic cell or by electrodialysis in an electrodialytic cell. The electrochemical cells generally contain an anode, a cathode, and one or more unit cells assembled for operational positioning between the anode and the cathode. A number of electrolytic and electrodialytic cells containing various unit cells and multiple unit cells are described herein which are useful in the process of the present invention. Multiple unit cells may be defined by a number of compartments between an anode and a cathode (see, for example, FIG. 3), or multiple unit cells may be defined by a number of compartments including an anode and cathode (see, for example, FIGS. 1B and 4B). Multiple unit cells including an anode and cathode may take a monopolar configuration (see, for example, FIG. 1B), or a bipolar configuration (see, for example, FIG. 4B). There is no particular limit to the number of unit cells which can be used. In one embodiment, electrochemical cells which are used according to the present invention contain from 1 to about 25 unit cells, and preferably from 1 to about 10 unit cells.

The unit cells may contain three or more compartments defined by the anode, cathode, two or more dividers or separators and optionally one or more bipolar membranes. Dividers or separators may be (1) nonionic microporous diffusion barriers such as screens, filters, diaphragms, etc., of controlled pore size or pore size distribution allowing certain ions to pass through the divider or separator, or (2) ionic dividers or separators such as anion selective membranes and cation selective membranes which are preferred since their use generally results in the production of hydroxide compounds of higher purity and in higher yield. The various dividers useful in the electrochemical cells used in the invention are described more fully below.

Electrochemical cells according to the invention contain at least three compartments; namely, a feed compartment, a water compartment and a recovery compartment. Optionally, electrochemical cells according to the invention may contain at least one pass compartment. In certain embodiments, an electrochemical cell according to the invention may have two or more of each of the compartments described above. In other embodiments, the electrochemical cell may have two or more of one or more of the compartments listed above. For example, in one embodiment, an electrochemical cell may have a feed compartment, two water compartments and a recovery compartment.

A solution is charged to each compartment. The solution may be aqueous based, alcohol based, an organic solution or combinations thereof. In a preferred embodiment, the solution charged into each compartment is an aqueous solution. The solution charged into the feed compartment contains the hydroxide compound to be recycled or purified at a certain concentration. The concentration of the hydroxide compound initially charged into the feed compartment is in the range from about 0.01M to about 1M. In another embodiment, the concentration of the hydroxide compound in the solution charged to into the feed compartment is from about 0.1M to about 0.5M. In electrochemical cells containing two or more feed compartments, the concentrations of the hydroxide compound in the solutions charged into the feed compartments may be the same or different for each feed compartment. The concentration of the hydroxide compound in the solution charged to the cell is from about 0.5% to about 50% by weight and more often between 2% and 5% by weight. The feed compartment, as the term implies, holds the solution containing a hydroxide compound which is to be recycled and processed by the electrochemical cell.

The water compartment contains a solution of an ionic compound at a certain concentration. The water compartment containing an ionic compound serves to maintain conductivity and enable lower operating cell voltages. An ionic compound is a chemical compound that ionizes in solution, such as an electrolyte. Examples of ionic compounds include salts, metal salts and acids or any compound which forms an anion and cation when dissolved in water. In a preferred embodiment, the ionic compound is the same as the hydroxide compound charged into the feed compartment. In another embodiment, the ionic compound is different from the hydroxide compound charged into the feed compartment. The concentration of the ionic compound in the water compartment is in the range from about 0.01M to about 2M. In a preferred embodiment, the concentration is from about 0.05M to about 1M. And in a most preferred embodiment, the concentration is from about 0.1M to about 0.5M. In electrochemical cells containing two or more water compartments, the concentrations of the ionic compound in the solutions charged into the water compartments may be the same or different for each water compartment.

The recovery compartment initially is charged with a solution and preferably an aqueous solution. The solution charged to the recovery compartment may or may not contain an ionic compound. After passing a current through the electrochemical cell, the hydroxide compound may be recovered or otherwise obtained from the recovery compartment at a certain concentration. After passing a current through the electrochemical cell, the concentration of the hydroxide compound in the recovery compartment is generally higher than the concentration of the hydroxide compound initially charged into the feed compartment. In one embodiment, the concentration of the hydroxide compound in the recovery compartment is above about 1M. In another embodiment, the concentration of the hydroxide compound in the recovery compartment is above about 1.5M. In a preferred embodiment, the concentration of the hydroxide compound in the recovery compartment is above about 2M. In electrochemical cells containing two or more recovery compartments, the concentrations of the hydroxide compound in the solutions recovered from the recovery compartments may be the same or different for each recovery compartment.

The pass compartment initially is charged with a solution and preferably an aqueous solution. The solution charged to the pass compartment may or may not contain an ionic compound. After passing a current through the electrochemical cell, the hydroxide compound passes through the pass compartment in embodiments where a pass compartment is used. Since most undesirable compounds do not pass through the pass compartment, the pass compartment serves to further purify the hydroxide compound.

Several embodiments of electrochemical cells which may be used in the invention will be described with reference to the figures. Although numerous embodiments of various electrochemical cells are described in the figures, it will be readily apparent to those skilled in the art that numerous embodiments not specifically described in the figures exist within the scope of the invention.

In one embodiment, an electrochemical cell is illustrated in FIG. 1A, which is a schematic representation of an electrochemical cell 10 containing a cathode 11, an anode 12, and in sequence beginning at the anode 12, an anion selective membrane 13 and a cation selective membrane 14. The electrochemical cell 10 illustrated in FIG. 1A contains three compartments; namely, a water compartment 15, a feed compartment 16, and a recovery compartment 17.

In operation of the electrochemical cell illustrated in FIG. 1A, a solution containing an ionic compound, such as a hydroxide compound, at a first concentration is charged to the water compartment. Water is charged to the recovery compartment. A solution containing a hydroxide compound, such as tetramethylammonium hydroxide, at a second concentration is charged to the feed compartment. An electrical potential is established and maintained between the anode and the cathode to produce a flow of current across the cell whereupon the quaternary ammonium cation is attracted towards the cathode and passes through the cation selective membrane 14 into the recovery compartment 17. The quaternary ammonium cation combines with hydroxide ions formed at the cathode to produce the desired tetramethylammonium hydroxide at a third concentration in the recovery compartment 17. Purified tetramethylammonium hydroxide at a third concentration is recovered from the recovery compartment 17.

Figure 1B:
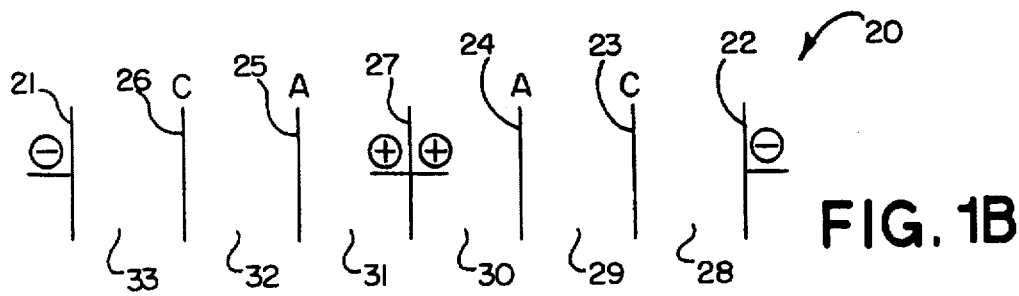
FIG. 1B is a schematic representation of an electrochemical cell containing a stack of two unit cells of the cell of FIG. 1A in a monopolar configuration.

In another embodiment, an electrochemical cell, and in particular a polyunit cell in a monopolar configuration similar to the cell of FIG. 1A, is illustrated in FIG. 1B, which is a schematic representation of an electrochemical cell 20 containing a cathode 21, a second cathode 22, an anode 27, and in sequence beginning at the second cathode 22, a first concentration cation selective membrane 23 a first anion selective membrane 24, a second anion selective membrane 25, and a second cation selective membrane 26. The electrochemical cell 20 illustrated in FIG. 1B contains six compartments; namely, a first recovery compartment 28, a first feed compartment 29, a first water compartment 30, a second water compartment 31, a second feed compartment 32, and a second concentration recovery compartment 33.

In operation of the electrochemical cell illustrated in FIG. 1B, a solution of an ionic compound at a first concentration is charged to the water compartments. Water is charged to the recovery compartments. A solution containing a hydroxide compound at a second concentration is charged to the feed compartments. An electrical potential is established and maintained between the anode and the cathodes to produce a flow of current across the cell whereupon a cation from the hydroxide compound is attracted to either the first cathode 21 or the second cathode 22 and passes through either the first cation selective membrane 23 or the second cation selective membrane 26 into either the recovery compartment 28 or the recovery compartment 33. The cation combines with hydroxide ions formed at the first cathode 21 or the second cathode 22 to produce the desired hydroxide compound at a third concentration in the recovery compartments 28 and 33. The hydroxide compound at a third concentration is recovered from the recovery compartments 28 and 33.

Figure 2:
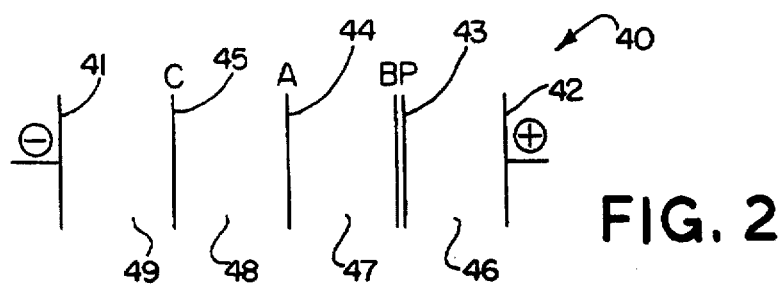
FIG. 2 is a schematic representation of a four-compartment electrochemical cell in accordance with the invention.

In another embodiment, an electrochemical cell is illustrated in FIG. 2, which is a schematic representation of an electrochemical cell 190 containing a cathode 41, an anode 42, and in sequence beginning at the anode 42, a bipolar membrane 43, an anion selective membrane 44, and cation selective membrane 45. The bipolar membrane 43 has an anion selective side (not shown) facing the anode and a cation selective side (not shown) facing the cathode. The electrochemical cell 40 illustrated in FIG. 2 contains four compartments; namely, a first water compartment 46, a second water compartment 47, a feed compartment 48, and a recovery compartment 49.

In operation of the electrochemical cell illustrated in FIG. 2, a solution of an ionic compound at a first concentration is charged to the water compartments. Water is charged to the recovery compartment. A solution containing a hydroxide compound at a second concentration is charged to the feed compartment. An electrical potential is established and maintained between the anode and the cathode to produce a flow of current across the cell whereupon a cation from the hydroxide compound is attracted towards the cathode 41 and passes through the cation selective membrane 45 into the recovery compartment 49. The cation combines with hydroxide ions formed at the cathode to produce the desired hydroxide compound at a third concentration in the recovery compartment 49. The hydroxide compound at a third concentration is recovered from the recovery compartment 49.

Figure 3:
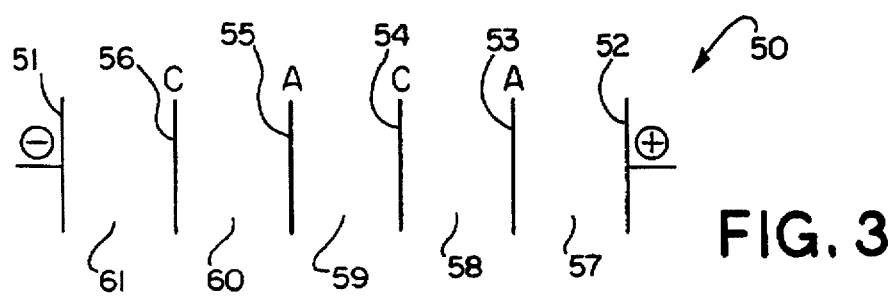
FIG. 3 is a schematic representation of a five-compartment electrochemical cell in accordance with the invention.

In another embodiment, an electrochemical cell is illustrated in FIG. 3, which is a schematic representation of an electrochemical cell 50 containing a cathode 51, an anode 52, and in sequence beginning at the anode 52, a first anion selective membrane 53, a first cation selective membrane 54, a second anion selective membrane 55, and a second cation selective membrane 56. The electrochemical cell 50 illustrated in FIG. 3 contains five compartments; namely, a water compartment 57, a first feed compartment 58, a first recovery compartment 59, a second feed compartment 60, and a second recovery compartment 61.

In operation of the electrochemical cell illustrated in FIG. 3, a solution containing an ionic compound at a first concentration is charged to the water compartment. Water is charged to the recovery compartments. A solution containing a hydroxide compound at a second concentration is charged to the feed compartments. An electrical potential is established and maintained between the anode and the cathode to produce a flow of current across the cell whereupon a cation of the hydroxide compound is attracted towards the cathode 51 and passes through either the first cation selective membrane 54 or the second cation selective membrane 56 into either the first recovery compartment 59 or the second recovery compartment 61. The cation combines with hydroxide ions formed at the cathode 51 to produce the desired hydroxide compound at a third concentration in the recovery compartment 61. Simultaneously, the cation attracted from the first feed compartment 58 combines with hydroxide ions which migrate from the second feed compartment 60 into the first recovery compartment 59 to produce the desired hydroxide compound at a third concentration in the first recovery compartment 59. The hydroxide compound at a third concentration is recovered from the recovery compartments 59 and 61.

Figure 4A:
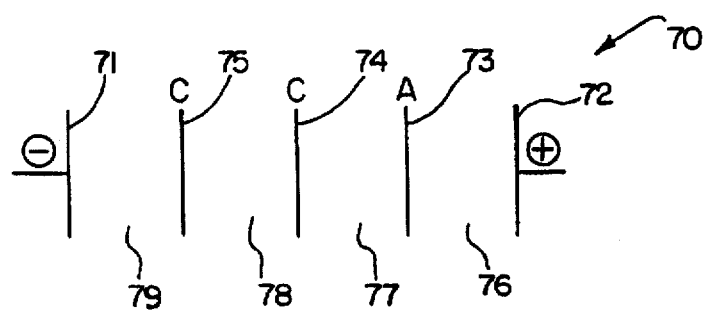
FIG. 4A is a schematic representation of another four-compartment electrochemical cell in accordance with the invention.

In another embodiment, an electrochemical cell is illustrated in FIG. 4A, which is a schematic representation of an electrochemical cell 70 containing a cathode 71, an anode 72, and in sequence beginning at the anode 72, an anion selective membrane 73, a first cation selective membrane 74, a second cation selective membrane 75. The first cation selective membrane 74 may be replaced with a nonionic divider. The electrochemical cell 70, illustrated in FIG. 4A contains four compartments; namely, a water compartment 76, a feed compartment 77, a pass compartment 78, and a recovery compartment 79.

In operation of the electrochemical cell illustrated in FIG. 4A, a solution containing an ionic compound at a first concentration is charged to the water compartment. Water is charged to the recovery and the pass compartments. A solution containing a hydroxide compound at a second concentration is charged to the feed compartment. An electrical potential is established and maintained between the anode and the cathode to produce a flow of current across the cell whereupon a cation of the hydroxide compound is attracted towards the cathode and passes through the first cation selective membrane 74 or the second cation selective membrane 75 into the recovery compartment 79. The cation combines with hydroxide ions formed at the cathode to produce the desired hydroxide compound at a third concentration in the recovery compartment 79. The hydroxide compound at a third concentration is recovered from the recovery compartment 79.

Figure 4B:
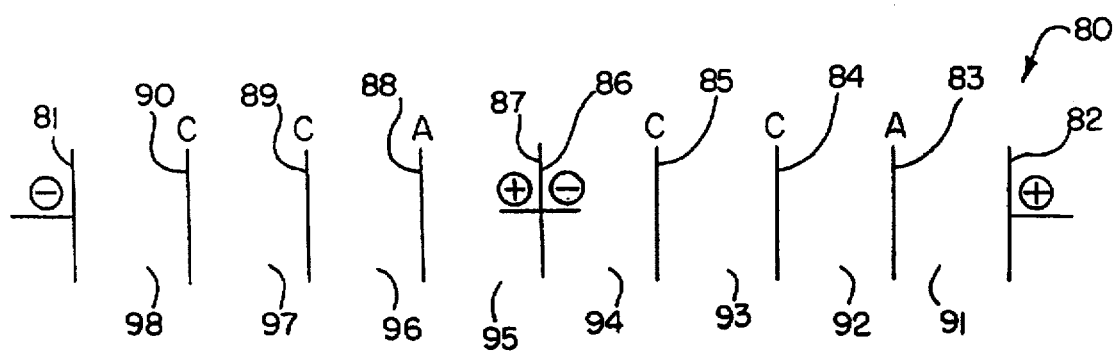
FIG. 4B is a schematic representation of an electrochemical cell containing a stack of two unit cells of the cell of FIG. 4A in a bipolar configuration.

In another embodiment, an electrochemical cell is illustrated in FIG. 4B which is a schematic representation of a polyunit cell in a bipolar configuration similar to the cell of FIG. 4A is an electrochemical cell 80 containing a first cathode 81, a first anode 82, and in sequence beginning at the first anode 82, a first anion selective membrane 83, a first cation selective membrane 84, a second cation selective membrane 85, a second cathode 86, a second anode 87, a second anion selective membrane 88, a third cation selective membrane 89, and a fourth cation selective membrane 90. Any of the cation selective membranes may be replaced with a nonionic divider. The electrochemical cell 80, illustrated in FIG. 4A contains eight compartments; namely, a first water compartment 91, a first feed compartment 92, a first pass compartment 93, and a first recovery compartment 94, a second water compartment 95, a second feed compartment 96, a second pass compartment 97, and a second recovery compartment 98.

In operation of the electrochemical cell illustrated in FIG. 4A, a solution containing an ionic compound at a first concentration is charged to the water compartments. Water is charged to the recovery and the pass compartments. A solution containing a hydroxide compound at a second concentration is charged to the feed compartments. An electrical potential is established and maintained between the anodes and the cathodes to produce a flow of current across the cell whereupon a cation of the hydroxide compound is attracted towards the cathode of each unit cell and passes through the first or third cation selective membranes 84 or 89 or the second or fourth cation selective membranes 85 or 90 into the recovery compartments 94 or 98. The cation combines with hydroxide ions formed at the cathodes to produce the desired hydroxide compound at a third concentration in the recovery compartments 94 and 98. The hydroxide compound at a third concentration is recovered from the recovery compartments 94 and 98.

Figure 5:
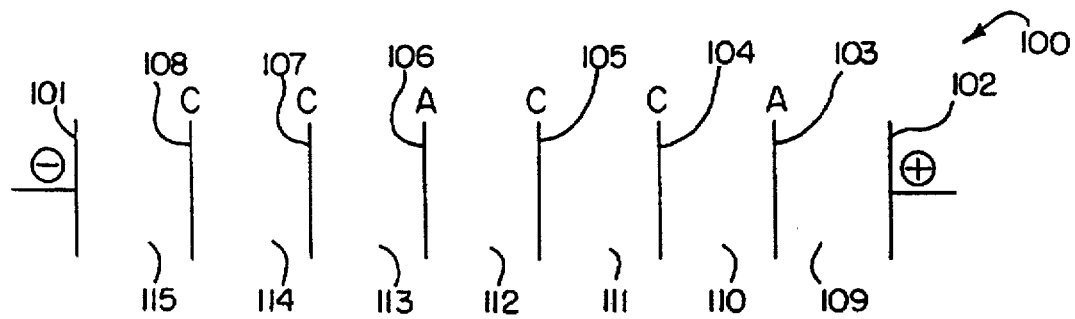
FIG. 5 is a schematic representation of a seven-compartment electrochemical cell in accordance with the invention.

In another embodiment, an electrochemical cell is illustrated in FIG. 5, which is a schematic representation of an electrochemical cell 100 containing a cathode 101, an anode 102, and in sequence beginning at the anode 102, an first anion selective membrane 103, a first cation selective membrane 104, a second cation selective membrane 105, a second anion selective membrane 106, a third cation selective membrane 107, and a fourth cation selective membrane 108. The first cation selective membrane 104 and the third cation selective membrane 107 may be replaced with a nonionic divider. The electrochemical cell 100, illustrated in FIG. 5 contains seven compartments; namely, a water compartment 109, a first feed compartment 110, a first pass compartment 111, and a first recovery compartment 112, a second feed compartment 113, a second pass compartment 114, and a second recovery compartment 115.

In operation of the electrochemical cell illustrated in FIG. 5, a solution containing an ionic compound at a first concentration is charged to the water compartment. Water is charged to the recovery and pass compartments. A solution containing a hydroxide compound at a second concentration is charged to the feed compartments. An electrical potential is established and maintained between the anode and the cathode to produce a flow of current across the cell whereupon a cation of the hydroxide compound is attracted towards the cathode and passes through one or more of the first cation selective membrane 104, the second cation selective membrane 105, the third cation selective membrane 107 and the fourth cation selective membrane 108 into either the first recovery compartment 112 or the second recovery compartment 115. In the first recovery compartment 112, the cation combines with hydroxide ions which migrated through the anion selective membrane 116 from the second feed compartment 113 to produce the desired hydroxide compound at a third concentration in the recovery compartment 112. The cation in recovery compartment 115 combine with hydroxide ions formed at the cathode to produce the desired hydroxide compound at a third concentration in the recovery compartment 115. The hydroxide compound at a third concentration is recovered from recovery compartments 112 and 115.

Figure 6:
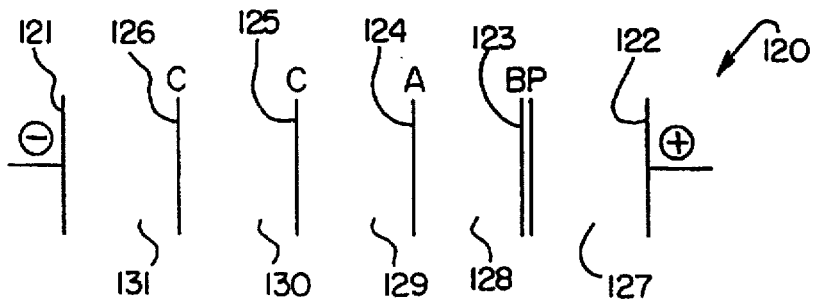
FIG. 6 is a schematic representation of another five-compartment electrochemical cell in accordance with the invention.

In another embodiment, an electrochemical cell is illustrated in FIG. 6, which is a schematic representation of an electrochemical cell 120 containing a cathode 121, an anode 122, and in sequence beginning at the anode 122, a bipolar membrane 123, an anion selective membrane 124, a first cation selective membrane 125, a second cation selective membrane 126. The first cation selective membrane 125 may be replaced with a nonionic divider. The bipolar membrane 123 has an anion selective side (not shown) facing the anode and a cation selective side (not shown) facing the cathode. The electrochemical cell 120 illustrated in FIG. 6 contains five compartments; namely, a first water compartment 127, a second water compartment 128, a feed compartment 129, a pass compartment 130, and a recovery compartment 131.

In operation of the electrochemical cell illustrated in FIG. 6, a solution containing an ionic compound at a first concentration is charged to the water compartments. Water is charged to the recovery and pass compartments. A solution containing a hydroxide compound at a second concentration is charged to the feed compartment. An electrical potential is established and maintained between the anode and the cathode to produce a flow of current across the cell whereupon a cation from hydroxide compound is attracted towards the cathode and passes through the first cation selective membrane 125 and second cation selective membrane 126 into the recovery compartment 131. The cation combines with hydroxide ions formed at the cathode to produce the desired hydroxide compound at a third concentration in the recovery compartment 131. The hydroxide compound at a third concentration is recovered from the recovery compartment 131.

In the embodiments of FIGS. 4–6, higher purity hydroxide compounds are obtained since the cations of the hydroxide compounds pass through two cation selective membranes resulting in lower contamination of the desired hydroxide by other anions such as chloride ion.

Since the desired product is the hydroxide compound, the recovery compartment contains a solution of water, alcohol, an organic liquid or a mixture of water and alcohol and/or an organic solvent provided that the recovery compartment contains sufficient water so that the desired hydroxide compound may form. The other compartments may contain water, alcohol, an organic liquid as described above, or a mixture of water and alcohol and/or an organic liquid.

Operation of the process of the present invention utilizing the electrochemical cells illustrated in FIGS. 1–6 generally is continuous and all of the liquids are continuously recirculated. Circulation is effected by pumping and/or by gas evolution. However, such electrochemical cells can be operated batchwise or in a continuous operation.

Various materials can be used as anodes in the electrochemical cells. For example, the anode may be made of metals such as titanium-coated electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides containing at least one oxide or mixed oxides of a noble metal such as platinum, iridium, ruthenium, palladium or rhodium. In one embodiment, the anode is a dimensionally stable anode such as an anode having a titanium base with ruthenium and/or iridium oxides thereon.

Various materials which have been used as cathodes in electrochemical cells can be included in the cells used in the above and other embodiments of the present invention. Cathode materials include nickel, iron, stainless steel, nickel plated titanium, graphite, carbon steel (iron) and alloys thereof etc. The term "alloy" is used in a broad sense and includes intimate mixtures of two or more metals as well as one metal coated onto another metal.

The electrochemical cell utilized in the process of the present invention contains at least two dividers or separators such as ionic selective membranes, and optionally at least one bipolar membrane. Compartments are defined as the area between two of: dividers and/or bipolar membranes and/or the anode and/or cathode. The dividers and/or bipolar membranes function as diffusion barriers and/or gas separators.

The dividers or separators which can be utilized in the present invention can be selected from a wide variety of microporous diffusion barriers, screens, filters, diaphragms, etc., which contain pores of the desired size allow cations of the hydroxide compound, such as onium cations, to migrate toward the cathode. The microporous dividers can be prepared from various materials including plastics such as polyethylene, polypropylene and Teflon, ceramics, etc. Microporous dividers such as nonionic dividers can be used, for example, in addition to the dividers listed in the Figures or in place of certain dividers, such as cation selective membranes 75 in FIG. 4A, 90 in FIG. 4B, 108 in FIG. 5, and 126 in FIG. 6. Specific examples of commercially available microporous separators include: Celanese Celgard and Norton Zitex. Microporous separators are particularly useful when the process of the present invention is utilized to purify the higher molecular weight hydroxides such as tetra n-butyl phosphonium hydroxide and tetra n-butyl ammonium hydroxide.

The cation selective membranes used in the cells and the process of the invention may be any of those which have been used in the electrochemical purification or recycling of hydroxide compounds. Preferably, the cation-exchange membranes should contain a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/ perfluorocarboxylic acid, perfluorocarbon polymer membranes such as sold by the E.I. dupont Nemours & Co. under the general trade designation "Nafion" such as DuPont's Cationic Nafion 902 membrane. Other suitable cation selective membranes include styrenedivinyl benzene copolymer membranes containing cation selective groups such as sulfonate groups, carboxylate groups, etc. Raipore Cationic R1010, (from Pall RAI), and NEOSEPTA CMH and NEOSEPTA CM1 membranes from Tokuyama Soda are useful particularly with the higher molecular quaternary compounds. The preparation and structure of cation selective membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

Any anion selective membrane may be utilized including membranes used in processes for the desalination of brackish water. Preferably, membranes should be selective with respect to the particular anions present in the cell (e.g., halide ions). The preparation and structure of anionic membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in the process of the present invention.

Among the anion selective membranes which may be utilized and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; NEOSEPTA AMH, NEOSEPTA ACM, NEOSEPTA AFN or NEOSEPTA ACLE-SP from Tokuyama Soda Co.; and Selemion AMV and Selemion AAV from Asahi Glass. In one embodiment, the Tosflex IE-SF 34 and NEOSEPTA AMH anion exchange membranes are preferred because of their stability in alkaline solutions, such as the hydroxide containing solutions which are involved in the process of the invention.

The bipolar membranes which may be used in the electrochemical cells are composite membranes containing three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in 4,116,889 (cast bipolar membranes). The bipolar membranes useful in the process of the present invention include NEOSEPTA BIPOLAR 1 by Tokuyama Soda, WSI BIPOLAR, and Aqualytics Bipolar membranes.

Electrochemical purifying or recycling of the mixture containing the hydroxide compound contained in the feed compartment is effected by applying a current (generally direct current) between the anode and the cathode. The current which is passed through the electrochemical cell generally is a direct current dictated by the design and performance characteristics of the cell which are readily apparent to those skilled in the art and/or can be determined by routine experimentation. Current densities between about 0.01 and about 4 amps per square inch are generally used, and current densities between about 0.3 and about 0.7 amps per square inch are preferred. Higher or lower current densities can be used for certain specific applications. The current density is applied to the cell for a period of time which is sufficient to result in the formation of the desired amount or concentration of the hydroxide compound in the recovery compartment.

During the electrochemical process, it is generally desirable that the temperature of the liquids within the cell be maintained within the range of from about 10° C. to about 80° C., preferably from about 30° C. to about 50° C., and particularly the temperature is maintained at about 40° C. during the electrochemical process. Also during the electrochemical process, it is generally desirable that the pH of the liquids within the cell is highly alkaline. In one embodiment, the pH is above about 13, and even above about 14. Since the claimed process is a purification process involving hydroxide, the pH changes as the process is practiced, and in particular, the pH generally increases as the process is practiced.

Although not wishing to be bound by any theory, operation of the electrochemical cells according to the invention is believed to be based, in part, on the migration of the cation of the hydroxide compound from the feed compartment to the recovery compartment as a result of the current applied.

The following examples illustrate the processes of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

An electrochemical cell according to FIG. 1A is assembled. The anode is made of titanium coated with ruthenium oxide and the cathode is made of nickel. An aqueous solution of tetramethylammonium hydroxide is charged into the water compartment where the concentration is maintained between 0.1M to 0.5M. Water is charged into the recovery compartment. A solution containing tetramethylammonium hydroxide at a concentration of about 0.2M and 50 ppm chloride is charged to the feed compartment. An electrical potential is applied thereby causing tetramethylammonium cations to migrate towards the cathode thereby producing tetramethylammonium hydroxide in the recovery compartment. The concentration of tetramethylammonium hydroxide in the recovery compartment is between 2M and 2.5M. The recovery compartment contains less than 1 ppm chloride.

EXAMPLE 2

An electrochemical cell according to FIG. 1A is assembled. The anode is made of titanium coated with iridium oxide and the cathode is made of stainless steel. An aqueous solution of tetramethylammonium hydroxide is charged into the water compartment where the concentration is maintained between 0.1M to 0.5M. Water is charged into the recovery compartment. A solution containing tetramethylammonium hydroxide at a concentration of about 0.2M, about 500 ppm nitrate and 50 ppm chloride is charged to the feed compartment. An electrical potential is applied thereby causing tetramethylammonium cations to migrate towards the cathode thereby producing tetramethylammonium hydroxide in the recovery compartment. The concentration of tetramethylammonium hydroxide in the recovery compartment is between 2M and 2.5M. The recovery compartment contains less than 10 ppm nitrate and less than 1 ppm chloride.

EXAMPLE 3

An electrochemical cell according to FIG. 1B is assembled. The anode is made of titanium coated with ruthenium oxide and the cathode is made of nickel. An aqueous solution of tetramethylammonium hydroxide is charged into the water compartments where the concentration is maintained between 0.1M to 0.5M. Water is charged into the recovery compartments. A solution containing spent tetramethylammonium hydroxide at a concentration of about 0.2M and 100 ppm chloride is charged to the feed compartment. An electrical potential is applied thereby causing tetramethylammonium cations to migrate towards the cathode thereby producing clean tetramethylammonium hydroxide in the recovery compartments. The concentration of tetramethylammonium hydroxide in the recovery compartments is between 2M and 2.5M. The recovery compartments contain less than 1 ppm chloride.

EXAMPLE 4

An electrochemical cell according to FIG. 1B is assembled. The anode is made of titanium coated with iridium oxide and the cathode is made of stainless steel. An aqueous solution of tetramethylammonium hydroxide is charged into the water compartments where the concentration is maintained between 0.1M to 0.5M. Water is charged into the recovery compartments. A solution containing spent tetramethylammonium hydroxide at a concentration of about 0.2M, about 1,000 ppm nitrate and 100 ppm ionic chloride is charged to the feed compartment. An electrical potential is applied thereby causing tetramethylammonium cations to migrate towards the cathode thereby producing clean tetramethylammonium hydroxide in the recovery compartments. The concentration of tetramethylammonium hydroxide in the recovery compartments is between 2M and 2.5M. The recovery compartments contain less than 10 ppm nitrate and less than 1 ppm ionic chloride.

EXAMPLE 5

An electrochemical cell according to FIG. 4A is assembled. The anode is made of titanium coated with ruthenium oxide and the cathode is made of nickel. An aqueous solution of tetramethylammonium hydroxide is charged into the water compartment where the concentration is maintained between 0.2M to 0.5M. Water is charged into the recovery and pass compartments. A solution containing impure tetramethylammonium hydroxide at a concentration of about 0.2M, about 2,000 ppm nitrate, 200 ppm chloride, and sodium and calcium impurities is charged to the feed compartment. An electrical potential is applied thereby causing tetramethylammonium cations to migrate towards the cathode thereby producing tetramethylammonium hydroxide having reduced metallic impurities in the recovery compartment. The concentration of tetramethylammonium hydroxide in the recovery compartment is between 2M and 2.5M. The recovery compartment contains less than 10 ppm nitrate and less than 1 ppm chloride.

EXAMPLE 6

An electrochemical cell according to FIG. 4A is assembled. The anode is made of titanium coated with iridium oxide and the cathode is made of stainless steel. An aqueous solution of tetramethylammonium hydroxide is charged into the water compartment where the concentration is maintained between 0.2M to 0.5M. Water is charged into the recovery and pass compartments. A solution containing tetramethylammonium hydroxide at a concentration of about 0.2M, about 2,000 ppm carbonate and 250 ppm chloride is charged to the feed compartment. An electrical potential is applied thereby causing tetramethylammonium cations to migrate towards the cathode thereby producing tetramethylammonium hydroxide in the recovery compartment. The concentration of tetramethylammonium hydroxide in the recovery compartment is between 2M and 2.5M. The recovery compartment contains less than 10 ppm carbonate and less than 1 ppm chloride.

EXAMPLE 7

An electrochemical cell according to FIG. 1B is assembled. The anode is made of titanium coated with ruthenium oxide and the cathode is made of nickel. An aqueous solution of tetramethylammonium hydroxide is charged into the water compartments where the concentration is maintained between 0.2M to 0.5M. Water is charged into the recovery compartments. A solution containing tetramethylammonium hydroxide at a concentration of about 0.2M and 400 ppm chloride is charged to the feed compartment. An electrical potential is applied thereby causing tetramethylammonium cations to migrate towards the cathode thereby producing tetramethylammonium hydroxide in the recovery compartments. The concentration of tetramethylammonium hydroxide in the recovery compartments is between 2M and 2.5M. The recovery compartments contain less than 1 ppm chloride.

EXAMPLE 8

An electrochemical cell according to FIG. 1B is assembled. The anode is made of titanium coated with iridium oxide and the cathode is made of stainless steel. An aqueous solution of tetramethylammonium hydroxide is charged into the water compartments where the concentration is maintained between 0.2M to 0.5M. Water is charged into the recovery compartments. A solution containing tetramethylammonium hydroxide at a concentration of about 0.2M, about 4,000 ppm carbonate and 500 ppm chloride is charged to the feed compartment. An electrical potential is applied thereby causing tetramethylammonium cations to migrate towards the cathode thereby producing tetramethylammonium hydroxide in the recovery compartments. The concentration of tetramethylammonium hydroxide in the recovery compartments is between 2M and 2.5M. The recovery compartments contain less than 10 ppm carbonate and less than 1 ppm chloride.

EXAMPLE 9

An electrochemical cell according to FIG. 1A is assembled. The anode is made of titanium coated with ruthenium oxide and the cathode is made of nickel. An aqueous solution of tetraethylammonium hydroxide is charged into the water compartment where the concentration is maintained between 0.1M to 0.5M. Water is charged into the recovery compartment. A solution containing tetraethylammonium hydroxide at a concentration of about 0.2M and 50 ppm chloride is charged to the feed compartment. An electrical potential is applied thereby causing tetraethylammonium cations to migrate towards the cathode thereby producing tetraethylammonium hydroxide in the recovery compartment. The concentration of tetraethylammonium hydroxide in the recovery compartment is between 2M and 2.5M. The recovery compartment contains less than 1 ppm chloride.

EXAMPLE 10

An electrochemical cell according to FIG. 4A is assembled. The anode is made of titanium coated with ruthenium oxide and the cathode is made of nickel. An aqueous solution of tetrabutylphosphonium hydroxide is charged into the water compartment where the concentration is maintained between 0.2M to 0.5M. Water is charged into the recovery and pass compartments. A solution containing tetrabutylphosphonium hydroxide at a concentration of about 0.2M and 100 ppm chloride is charged to the feed compartment. An electrical potential is applied thereby causing tetrabutylphosphonium cations to migrate towards the cathode thereby producing tetrabutylphosphonium hydroxide in the recovery compartment. The concentration of tetrabutylphosphonium hydroxide in the recovery compartment is between 2M and 2.5M. The recovery compartment contains less than 1 ppm chloride.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for purifying solutions containing a hydroxide compound, comprising the steps of:
   (A) providing an electrochemical cell comprising an anode, a cathode, a cation selective membrane and an anion selective membrane, wherein the cation selective membrane is positioned between the cathode and the anion selective membrane, and the anion selective membrane is positioned between the cation selective membrane and the anode, thereby defining a feed compartment between the cation selective membrane and the anion selective membrane, a recovery compartment between the cathode and the cation selective membrane, and a water compartment between the anion selective membrane and the anode;
   (B) charging a solution of an ionic compound at a first concentration to the water compartment, and water to the recovery compartment;
   (C) charging a solution of the hydroxide compound at a second concentration to the feed compartment;
   (D) passing a current through the cell to produce the hydroxide compound at a third concentration in the recovery compartment; and
   (E) recovering hydroxide compound from the recovery compartment.

2. The process of claim 1, wherein the electrochemical cell further comprises a bipolar membrane positioned between the anion selective membrane and the anode, thereby defining a recovery compartment between the cation selective membrane and the cathode, a feed compartment between the anion selective membrane and the cation selective membrane, a first water compartment between the bipolar membrane and the anion selective membrane, and a second water compartment between the anode and the bipolar membrane, wherein the solution of an ionic compound is charged to each water compartment.

3. The process of claim 1, wherein the electrochemical cell further comprises a second cation selective membrane positioned between the anion selective membrane and the anode, and a second anion selective membrane positioned between the second cation selective membrane and the anode, thereby defining a first recovery compartment between the cation selective membrane and the cathode, a first feed compartment between the anion selective membrane and the cation selective membrane, a second recovery compartment between the second cation selective membrane and the anion selective membrane, a second feed compartment between the second anion selective membrane and the second cation selective membrane, and a water compartment between the anode and the second anion selective membrane, wherein water is charged to each recovery compartment and the solution of the hydroxide compound at a second concentration is charged to each feed compartment.

4. The process of claim 1, wherein the electrochemical cell further comprises a second cation selective membrane positioned between the cation selective membrane and the cathode, thereby defining a water compartment between the anion selective membrane and the anode, a feed compartment between the cation selective membrane and the anion selective membrane, a pass compartment between the second cation selective membrane and the cation selective membrane, and a recovery compartment between the cathode and the second cation selective membrane, wherein water is charged to the pass compartment.

5. The process of claim 1, wherein the electrochemical cell further comprises a second cation selective membrane positioned between the cation selective membrane and the cathode, a third cation selective membrane positioned between the anion selective membrane and the anode, a fourth cation selective membrane positioned between the third cation selective membrane and the anode, and a second anion selective membrane positioned between the fourth cation selective membrane and the anode, thereby defining a first recovery compartment between the second cation selective membrane and the cathode, a first pass compartment between the cation selective membrane and the second cation selective membrane, a first feed compartment between the anion selective membrane and the cation selective membrane, a second recovery compartment between the third cation selective membrane and the anion selective membrane, a second pass compartment between the fourth cation selective membrane and the third cation selective membrane, a second feed compartment between the second anion selective membrane and the fourth cation selective membrane, and a water compartment between the anode and the second anion selective membrane, wherein water is charged to each recovery compartment and each pass compartment and the solution of the hydroxide compound at a second concentration is charged to each feed compartment.

6. The process of claim 1, wherein the electrochemical cell further comprises a bipolar membrane positioned between the anion selective membrane and the anode, and a second cation selective membrane positioned between the cation selective membrane and the cathode, thereby defining a first water compartment between the bipolar membrane and the anode, a second water compartment between the anion selective membrane and the bipolar membrane, a feed compartment between the cation selective membrane and the anion selective membrane, a pass compartment between the second cation selective membrane and the cation selective membrane, and a recovery compartment between the cathode and the second cation selective membrane, wherein the solution of the ionic compound is charged to each water compartment and water is charged to the pass compartment.

7. The process of claim 1, wherein the first concentration is between about 0.1M to about 0.5M.

8. The process of claim 1, wherein the third concentration is higher than the second concentration.

9. The process of claim 1, wherein the third concentration is above about 2M.

10. The process of claim 1, wherein the hydroxide compound is a quaternary alkyl ammonium hydroxide.

11. The process of claim 1, wherein the hydroxide compound is a quaternary ammonium hydroxide, a quaternary phosphonium hydroxide or a tertiary sulfonium hydroxide.

12. The process of claim 1, wherein the hydroxide compound is tetramethyl ammonium hydroxide.

13. A process for purifying solutions containing quaternary ammonium hydroxide, comprising the steps of:
   (A) providing an electrochemical cell comprising an anode, a cathode and one or more unit cells assembled for operational positioning between the anode and the cathode, each unit cell comprising;

(A-1) three compartments defined by, in sequence beginning at the anode, an anion selective membrane and a cation selective membrane;

(A-2) four compartments defined by, in sequence beginning at the anode, an anion selective membrane, a first cation selective membrane and a second cation selective membrane; or (A-3) four compartments defined by, in sequence beginning at the anode, a bipolar membrane, an anion selective membrane, and a cation selective membrane;

(B) charging a solution of an ionic compound at a first concentration to the compartment in each unit cell formed by the anion selective membrane and anode, the anion selective membrane and bipolar membrane, and the cathode and bipolar membrane, and charging water to the compartment in each unit cell formed by the cathode and cation selective membrane, the bipolar membrane and cation selective membrane, and the cation selective membrane and cation selective membrane;

(C) charging a solution of the quaternary ammonium hydroxide at a second concentration to the compartment in each unit cell formed by the cation selective membrane and anion selective membrane, and the cation selective membrane and anode;

(D) passing a current through the cell to produce quaternary ammonium hydroxide at a third concentration in the compartment in each unit cell formed by the cathode and cation selective membrane; and (E) recovering quaternary ammonium hydroxide from the compartments in each unit cell formed by the cathode and cation selective membrane.

14. The process of claim 13, wherein the first concentration is between about 0.1M to about 0.5M.

15. The process of claim 13, Wherein the third concentration is higher than the second concentration.

16. The process of claim 15, wherein the ionic compound is same as the hydroxide compound.

17. The process of claim 13, wherein the third concentration is above about 2M.

18. The process of claim 13, wherein the electrochemical cell comprises at least one unit cell defined by (A-1).

19. The process of claim 13, wherein the electrochemical cell comprises at least one unit cell defined by (A-2).

20. The process of claim 13, wherein the electrochemical cell comprises at least one unit cell defined by (A-3).

21. The process of claim 13, wherein the quaternary ammonium hydroxide is tetramethyl ammonium hydroxide.

* * * * *